US012163620B2

(12) United States Patent
Arnold et al.

(10) Patent No.: US 12,163,620 B2
(45) Date of Patent: *Dec. 10, 2024

(54) ADJUSTABLE BOTTLE SUPPORT

(71) Applicant: Keymed (Medical & Industrial Equipment) Limited, Southend-on-Sea (GB)

(72) Inventors: Adam Arnold, Southend-on-Sea (GB); Jordan Jowitt, Southend-on-Sea (GB); Timothy Roberts, Southend-on-Sea (GB); Nicholas MacMillan, Southend-on-Sea (GB); Nevzat Atakan, Southend-on-Sea (GB)

(73) Assignee: Keymed (Medical & Industrial Equipment) Limited, Southend-on-Sea (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/503,640

(22) Filed: Oct. 18, 2021

(65) Prior Publication Data

US 2022/0128191 A1    Apr. 28, 2022

(30) Foreign Application Priority Data

Oct. 22, 2020 (GB) .................................... 2016779
Sep. 6, 2021 (CN) ......................... 202111037935.3

(51) Int. Cl.
*B65D 23/00* (2006.01)
*F16M 11/20* (2006.01)
*A61J 1/16* (2023.01)

(52) U.S. Cl.
CPC ....... *F16M 11/2021* (2013.01); *B65D 23/001* (2013.01); *A61J 1/16* (2013.01)

(58) Field of Classification Search
CPC ......... A61J 9/0661; A61J 1/16; B65D 23/001; B65D 11/105; B65D 11/10; F16M 11/2021; A47G 23/02; A47G 23/0241
(Continued)

(56) References Cited

U.S. PATENT DOCUMENTS 3,627,244 A * 12/1971 Nicholas ............... A61J 9/0638
248/103
4,735,388 A * 4/1988 Marks ................... A61J 9/0638
248/103
(Continued)

FOREIGN PATENT DOCUMENTS

CN    202061091 U    12/2011
CN    203075219 U    7/2013
(Continued)

OTHER PUBLICATIONS

European Patent Office, Extended European Search Report in European Patent Application No. 21200715.7, 6 pp. (Mar. 18, 2022).

(Continued)

*Primary Examiner* — Alfred J Wujciak
(74) *Attorney, Agent, or Firm* — Leydig, Voit & Mayer, Ltd.

(57) ABSTRACT

An adjustable bottle support for a pump used in medical procedures comprises first and second support members pivotally connected together. The first and second support members can be moved between a first position in which they are aligned and level, and a second position in which the second support member is tilted relative to the first support member, to enable the support to hold different configurations of bottle.

14 Claims, 9 Drawing Sheets

(58) Field of Classification Search
USPC .... 248/102, 103, 104, 105, 106, 310, 311.2,
248/458, 455, 454, 447, 457, 905, 130,
248/133, 134, 135, 136, 137, 138, 139,
248/140, 141, 142, 144, 149, 349.1,
248/346.06, 346.03; 215/399, 395;
220/737, 4.22, 4.21, 23.4, 23.2
See application file for complete search history.

(56) References Cited

U.S. PATENT DOCUMENTS

| | | | |
|---|---|---|---|
| 6,098,834 A * | 8/2000 | Hatsumoto | A47G 19/2272 220/756 |
| 7,748,417 B2 * | 7/2010 | Arcuri | B67D 1/127 141/192 |
| 8,118,318 B1 * | 2/2012 | Chauza | B62B 1/16 280/47.3 |
| 2005/0035167 A1 | 2/2005 | Threet et al. | |
| 2014/0330205 A1 | 11/2014 | Tian | |
| 2018/0228697 A1 | 8/2018 | Dedvukaj et al. | |
| 2019/0061295 A1 * | 2/2019 | Ooshima | B29C 73/166 |
| 2022/0125679 A1 * | 4/2022 | Arnold | A61J 1/16 |

FOREIGN PATENT DOCUMENTS

| | | |
|---|---|---|
| CN | 203408257 U | 1/2014 |
| CN | 111135389 A | 5/2020 |
| WO | WO 96/24396 A1 | 8/1996 |

OTHER PUBLICATIONS

United Kingdom Intellectual Property Office, Search Report in United Kingdom Patent Application No. GB2016779.7, 1 p. (Mar. 16, 2021).

* cited by examiner

ADJUSTABLE BOTTLE SUPPORT

CROSS-REFERENCE TO RELATED APPLICATIONS

This application claims priority to Great Britain Patent Application No. GB 2016779.7, filed Oct. 22, 2020, which is incorporated by reference herein in its entirety for all purposes.

BACKGROUND

The present invention relates to an adjustable support or holder for medical equipment. In particular, the support is intended to support a bottle on a peristaltic pump, which is used to supply liquid from the bottle for a medical procedure such as an endoscopy.

Peristaltic pumps for medical procedures are frequently mounted on a shelf of a moveable workstation or trolley which also carries other equipment. Therefore, space is relatively limited. Typically, liquid is provided in a standard 1 litre disposable bottle which may be cylindrical or square in cross-section and is mounted on a support fixed to the side of the pump. However, for some procedures bottles of larger capacity are desired but cannot fit on a support intended for the standard bottles. There is a need to support various different sizes and configurations of bottle adjacent to the pump within the limited space available, ensuring the bottle is secure but easily accessible so that it can be replaced when empty.

SUMMARY

The present invention provides an adjustable bottle support for a pump, comprising a first support member, an attachment arm extending from the first support member, and a second support member secured to the attachment arm for pivotal movement relative to the first support member between a first position in which the two support members are aligned and level with one another and a second position in which the second support member is tilted relative to the first support member and slopes upwardly in a direction away from the first support member. The bottle support of the invention is therefore easily adjustable in order to accommodate different shapes and sizes of bottle.

Preferably, the first and second support members each comprise a flat base with front, rear and side edges, wherein in the first position, the front edge of the first support member and the rear edge of the second support member are adjacent and level with each other, the second support member is rotatable about a pivot axis between its front and rear edges, and in the second position the rear edge of the second support member is lower than the front edge of the first support member. Preferably, the first support member further comprises a downward sloping wall depending from the front edge. In the second position, the angle between the base of the second support member and the downward sloping wall of the first support member may be approximately 90 degrees. These features allow a smaller bottle to be located securely on the holder.

The first support member may further comprise a raised wall on the rear and at least one side edge, and the second support member may further comprise side walls on opposed side edges. The walls help to position and retain a bottle on the holder.

In one embodiment the pivot mechanism comprises three pivot pins extending from the attachment arm and arranged in a triangular configuration, the pivot axis of the second support member passes through the centre of the triangular configuration, and a side wall of the second support member comprises three arcuate slots centred on the pivot axis, wherein each pivot pin extends through one of the slots.

Preferably each slot comprises first and second ends and a notch is formed at each end for receiving a pivot pin in the first and second positions respectively. The notches are preferably positioned such that in the first and second positions the weight of the second support member acts to retain each pin in a notch.

In another embodiment, the pivot mechanism comprises a pivot axle extending from the attachment arm on which the second support member is rotatably mounted, and a detent on the second support member selectively engageable with the attachment arm at first and second locations.

Preferably the detent comprises a resilient arm on the second support member with a projection selectively engageable with first and second openings in the attachment arm.

The resilient arm may further comprise a grip portion protruding from the arm and operable by a user to selectively engage and disengage the projection with the first and second openings in the attachment arm.

Optionally, the second support member further comprises a heating device operable to heat fluid in a bottle supported thereon.

In addition to, or instead of, the pivot mechanisms described above, the adjustable bottle support may further comprise a flap attached to the second support member and moveable to a deployed position to hold the second support member in the second position.

DESCRIPTION OF DRAWINGS

The invention will now be described in detail, by way of example only, with reference to the accompanying drawings in which.

DETAILED DESCRIPTION

Figure 1:
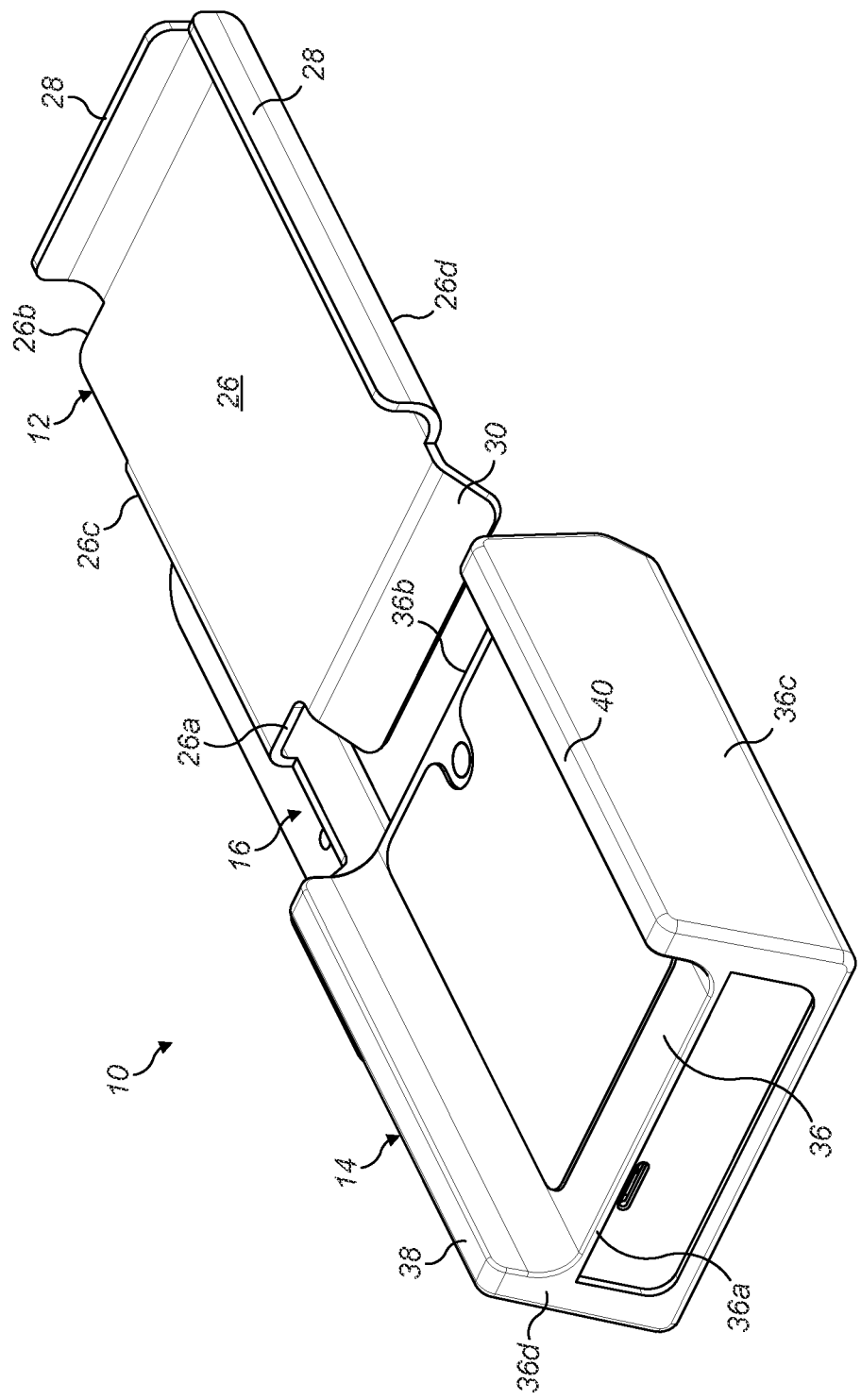
FIG. 1 shows an adjustable support of the present invention in a first, flat orientation.
Figure 2:
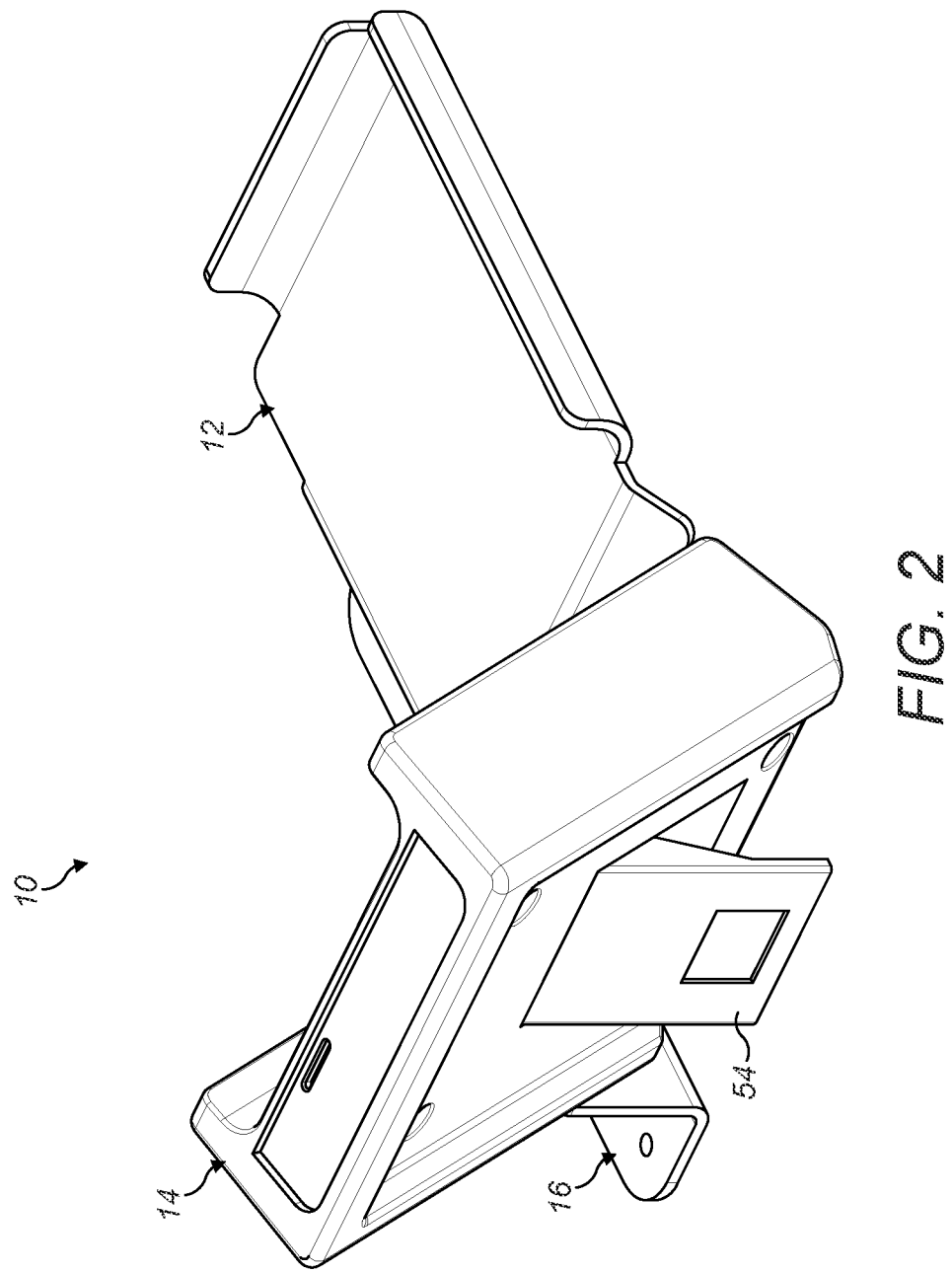
FIG. 2 shows the support of FIG. 1 in a second, folded configuration.

An adjustable equipment holder 10 in accordance with the present invention comprises a first, fixed support tray 12, a second, moveable support tray 14 and an attachment arm 16. The attachment arm 16 is used for attaching the holder 10 to a pump body 18 (which is shown schematically in FIGS. 3 and 4) and as an attachment point for a pivot mechanism 20 which allows the second tray 14 to move between first and second positions. In the first position, the moveable tray 14 is flat and level with the fixed tray 12 as shown in FIG. 1. In the second position, the moveable tray 14 is tilted, for example at an angle of about 50 degrees to the horizontal, and slopes upwardly in a direction away from the fixed tray 12 as shown in FIG. 2. In this position, the rear edge of the moveable tray 14 is lower than the front edge of the fixed tray 12

Figure 3:
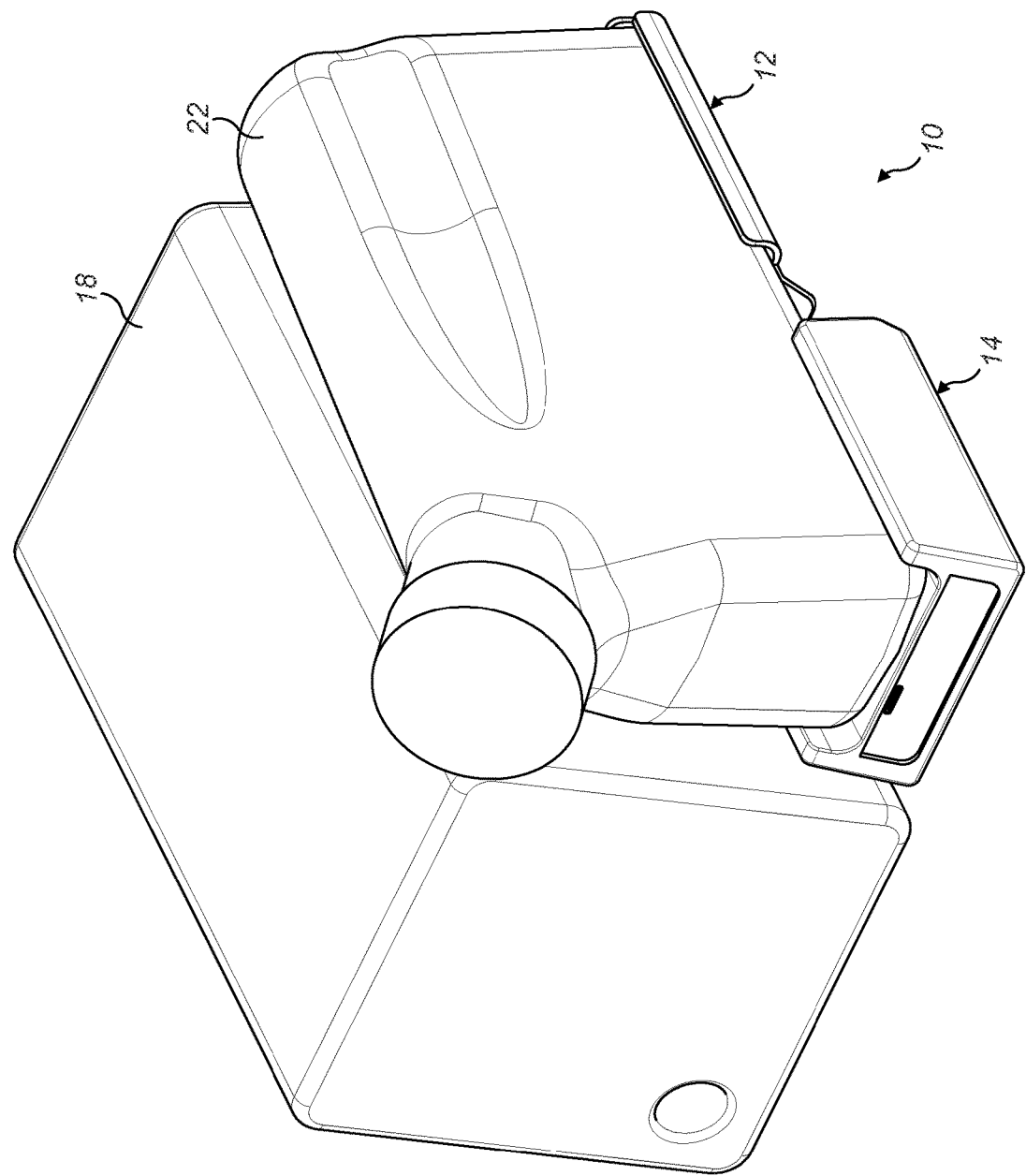
FIG. 3 shows a pump body and an adjustable support of the present invention in the first flat orientation with a bottle supported thereon.

As shown in FIG. 3, when the holder 10 is in the first, flat position, a larger bottle 22, or other item of equipment, can be supported across the surface of both the first, fixed tray 12 and second, moveable tray 14.

Figure 4:
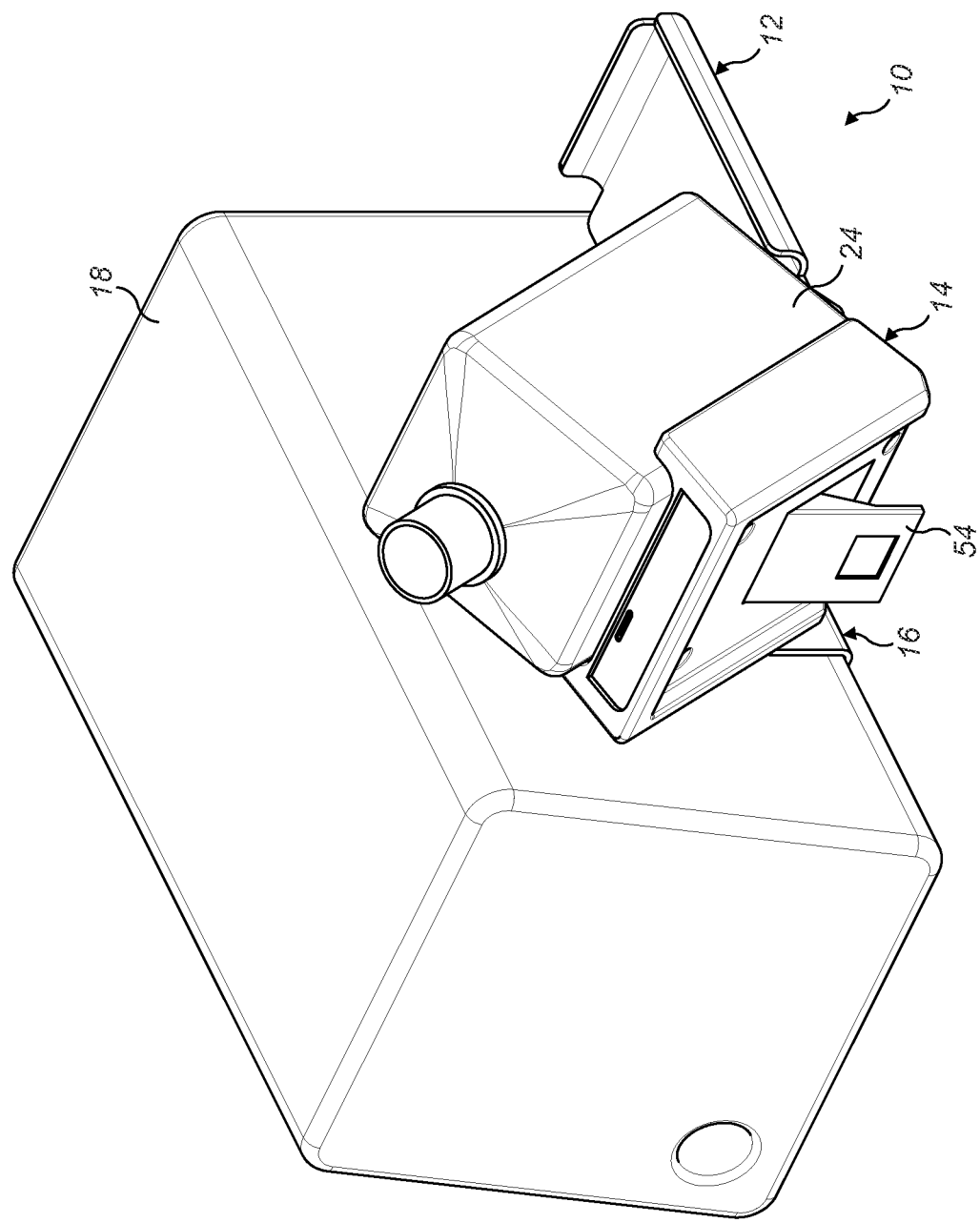
FIG. 4 shows a pump body and an adjustable support of the present invention in the second, folded orientation supporting a different form of bottle.

As shown in FIG. 4, in the second, tilted position a smaller bottle 24, or other item of equipment, can be supported. The side of the bottle 24 rests against the surface of the moveable tray 14. The base of the bottle 24 rests against the front edge of the fixed tray 12.

The first, fixed tray 12 comprises a flat base 26 with front, rear and opposing side edges 26*a-d*. The rear edge 26 *b* and the side edge 26*c* which will be furthest from the pump body 18 in use, are preferably formed with upturned walls 28. The front edge 26*a* is formed with a downward sloping wall 30. Preferably, this slopes at approximately 40 degrees to the horizontal.

Figure 5:
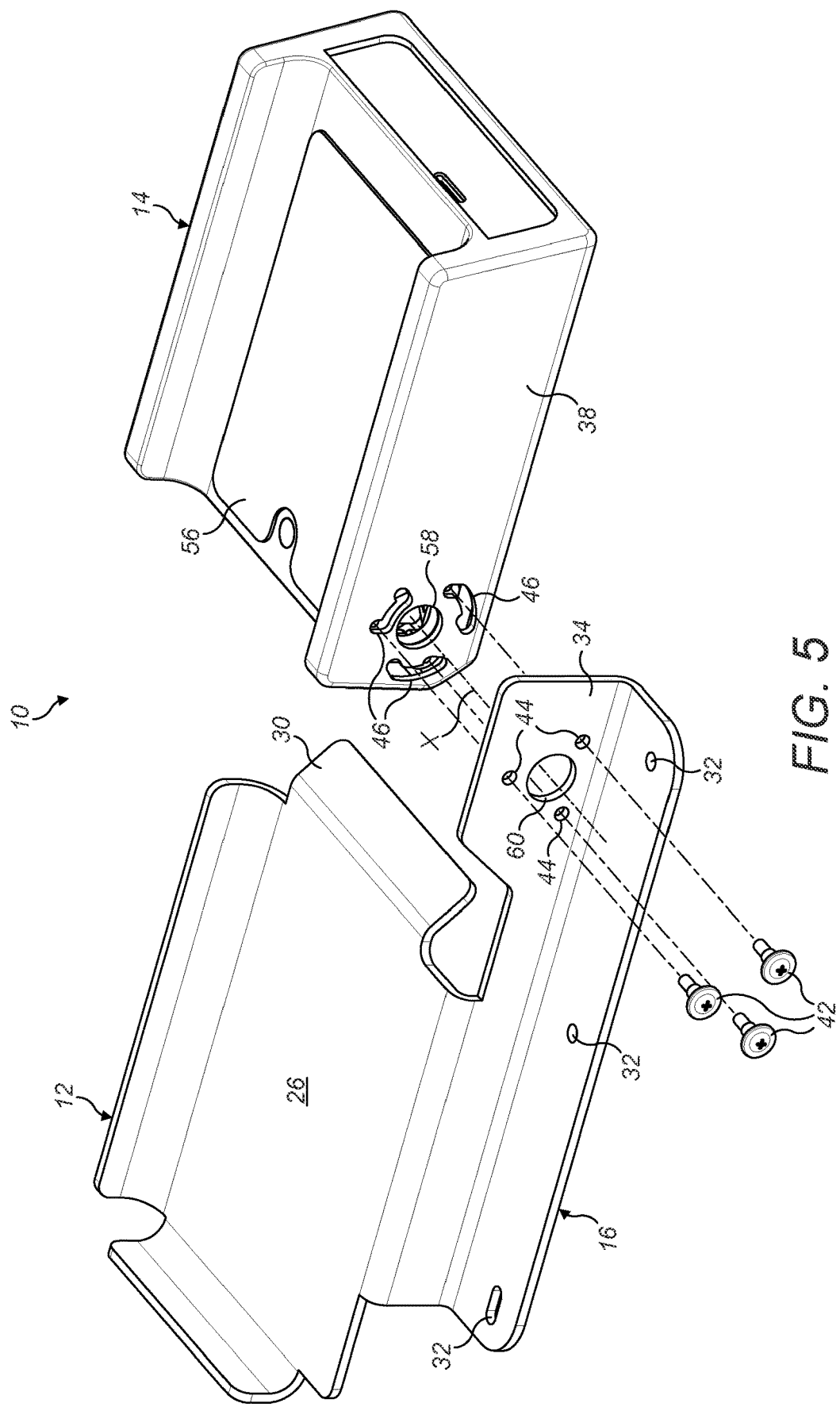
FIG. 5 is an exploded view of an adjustable support with one embodiment of pivot mechanism.

The attachment arm 16 for attaching the holder 10 to a pump body 18 extends from the other side edge 26*d*. This is best seen in FIG. 5. The fixed tray 12 and attachment arm 16 may be formed integrally, for example pressed from sheet metal or as a one-piece plastic moulding. Alternatively, they may be formed separately and bonded or mechanically joined together. The attachment arm 16 is shaped to locate against part of the pump body 18 and includes fixing holes 32 for attachment devices such as screws.

The attachment arm 16 includes a forward extension 34, protruding beyond the front edge 26*a* and sloping wall 30 of the fixed tray 12. This provides an attachment point for the moveable tray 14 and pivot mechanism 20.

The moveable tray 14 also comprises a flat base 36 with front, rear and opposing side edges 36*a-d*. First and second side walls 38, 40 are provided on the side edges 36*c, d*. These extend above and below the base 36. In use, the moveable tray 14 is mounted with the first side wall 38 adjacent to the forward extension 34 of the attachment arm 16 and pivots relative thereto. The moveable tray 14 optionally includes a heating device which is described further below. The moveable tray 14 may be formed as plastic moulding, particularly when a heating device is to be included. However, it may be formed from other materials, for example pressed from sheet metal.

The pivot mechanism 20 allows the moveable support 14 to pivot between the flat and angled positions and retains the moveable tray in each position without the need for additional components or tools.

In a first embodiment seen in FIG. 5, the pivot mechanism 20 comprises three pivot pins 42 arranged in a triangular configuration. The pins 42 pass though openings 44 in the attachment arm 16 and through arcuate slots 46, 48, 50 in the first side wall 38 of the movable tray 14 and are fixed to a plate 52 mounted beneath the base 36 of the moveable tray 14. The attachment arm 16, pins 42 and the plate 52 all remain stationary and the tray 14 is able to rotate relative to them by sliding the arcuate slots 46, 48, 50 over the pins 42. The pivot axis X passes through the centre of the triangle defined by the pins 42.

As best seen in FIGS. 6A-D, each slot 46 comprises an arcuate portion which forms part of a circle centred on the pivot axis X. Each slot 46 also has a notch 48, 50 at each end. The uppermost slot has notches 48, 50 extending outwardly away from the pivot axis X. The two lower slots have notches 48, 50 extending inwardly towards the pivot axis X. FIGS. 6A to 6D illustrate how the pins 42 move relative to the slots 46 as the moveable tray 14 is pivoted between the flat and angled orientations.

Figure 6A:
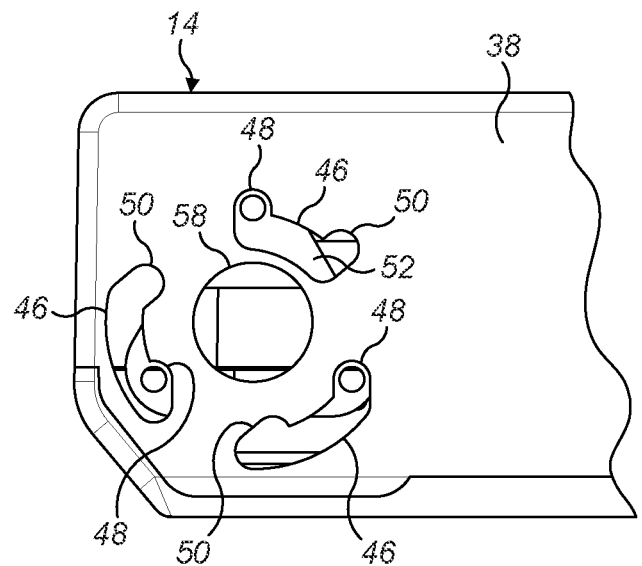
FIGS. 6A to 6D are detailed views of the pivot mechanism of the support of FIG. 5.
Figure 6B:
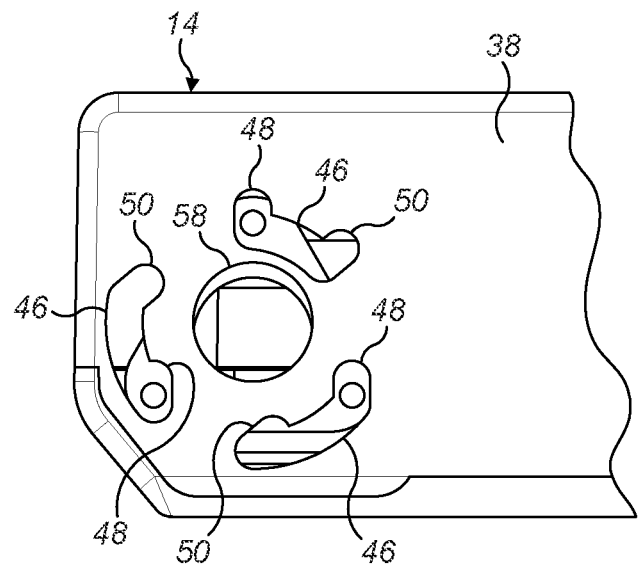
Figure 6C:
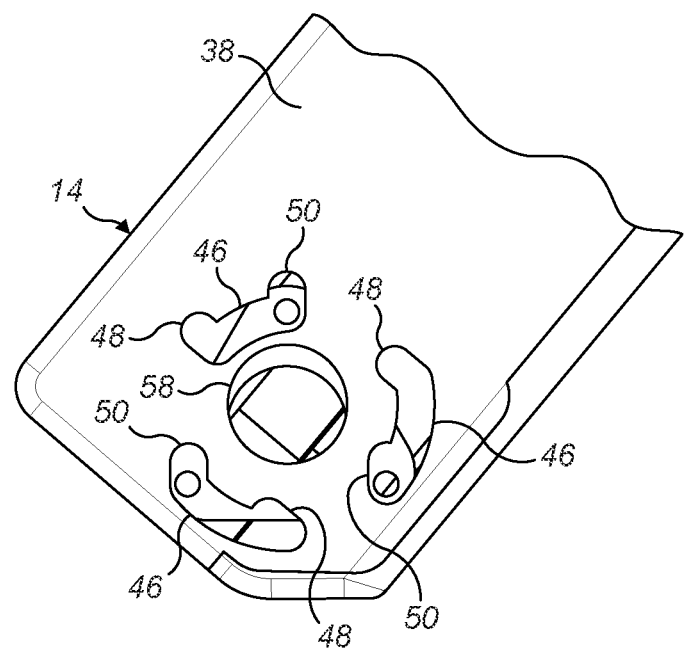
Figure 6D:
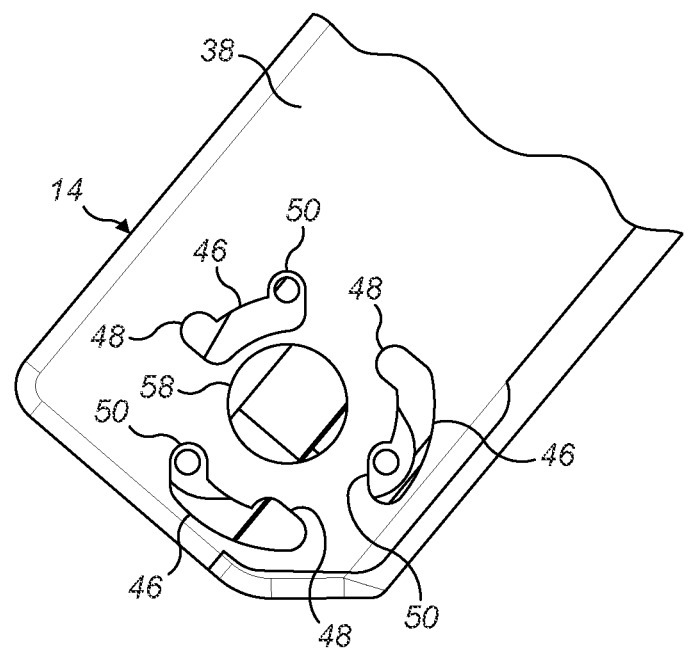

In a first position shown in FIG. 6A, each pivot pin 42 is located in a notch 48 at a first end of its respective slot 46 and the moveable tray 14 is locked in the flat position. In order to change the orientation of the tray 14, the tray 14 is first raised in order to move each pin 42 out of the notch 48 into the arcuate portion of its slot 46, as seen in FIG. 6B. The tray 14 can then be rotated (anticlockwise in the figures) such that each pin 42 moves along the arcuate portion of the slot 46 to the other end, as shown in FIG. 6C. The moveable tray 14 is then lowered in order to engage each pin 42 in the notch 50 at that second end of the slot 46, as shown in FIG. 6D.

Thus, in both the flat and tilted positions, the weight of the tray 14 itself (and any bottle supported on it) pushing the tray 14 downwards acts to retain the pins 42 in the notches 48, 50. To move the tray 14 it is only necessary to slightly raise it in order to move each pin 42 out of the relevant notch and into the arcuate portion of the slot 46.

The pivot axis X is located forward of the rear edge 36*b* of the moveable tray 14. Therefore, in the tilted position, the rear edge 36*b* of the moveable tray 14 is lower than the front edge 26*a* and base 26 of the fixed tray 12. When a smaller bottle 24 is positioned on the holder 10 as in FIG. 4, the side of the bottle 24 rests against the base 36 of the moveable tray 14 and the base of the bottle 24 rests against the sloping wall 30 at front edge of the fixed tray 12. The angle between the tilted moveable tray 14 and the sloping wall 30 is preferably approximately 90 degrees, to fit against the side and the bottom of the bottle 24. This locates the bottle 24 more securely than if the rear edge 36*b* of the moveable tray 14 remained at the same level as the base 26 of the fixed tray 12. Supporting the bottle 24 in the tilted position also makes it easier to ensure it can be fully emptied.

As mentioned above, the moveable tray 14 optionally includes a heating device 56 to warm fluid in a bottle resting thereon. Warming the fluid is desirable in many medical procedures. The heating device 56 may comprise an electrically heated plate set into the base 36 of the moveable tray 14. Wires or cables connecting the heating device 56 to a power supply may be routed out of the moveable tray 14 through an aperture 58 in the side wall 38 and a corresponding aperture 60 in the bracket 16. These apertures 58, 60 are located in the centre of the triangular configuration of the pivot pins 42 and arcuate slots 46, and are therefore centred on the pivot axis X and do not obstruct the pivoting movement of moveable tray 14. The moveable tray 14 optionally also includes an illumination device to illuminate a bottle mounted on the holder 10. As the bottles may be translucent or transparent, this helps to show the amount of fluid in the bottle so that it is easy to tell when the bottle is nearly empty and replacement is required.

In a second embodiment, the overall structure of the holder 10 is the same as that described above, except for the pivot mechanism 20. In this case, the pivot mechanism 20 comprises a pivot pin connecting the moveable tray 14 to the attachment arm 16 and a biased or sprung detent on the moveable tray 14, selectively engageable with the attachment arm 16 at first and second locations, to retain the moveable tray 14 in the flat and tilted positions.

Figure 7A:
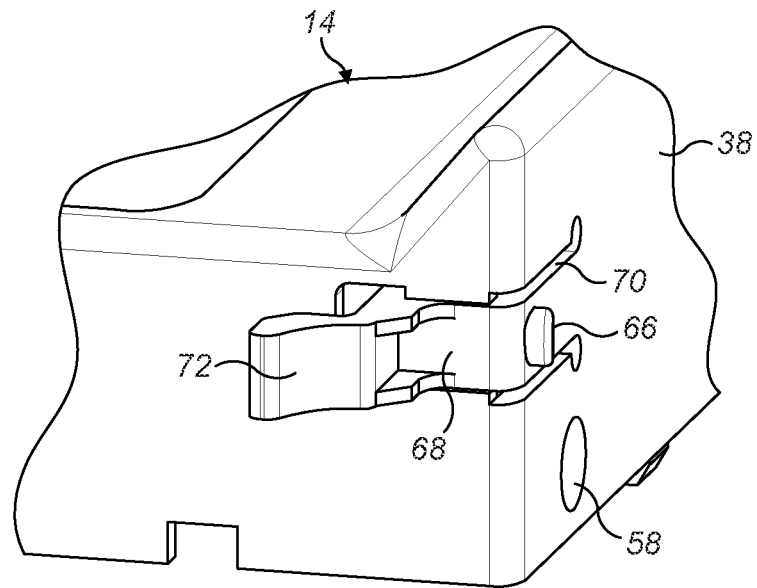
FIGS. 7A and 7B are detailed views of part of a second embodiment of the pivot mechanism.
Figure 7B:
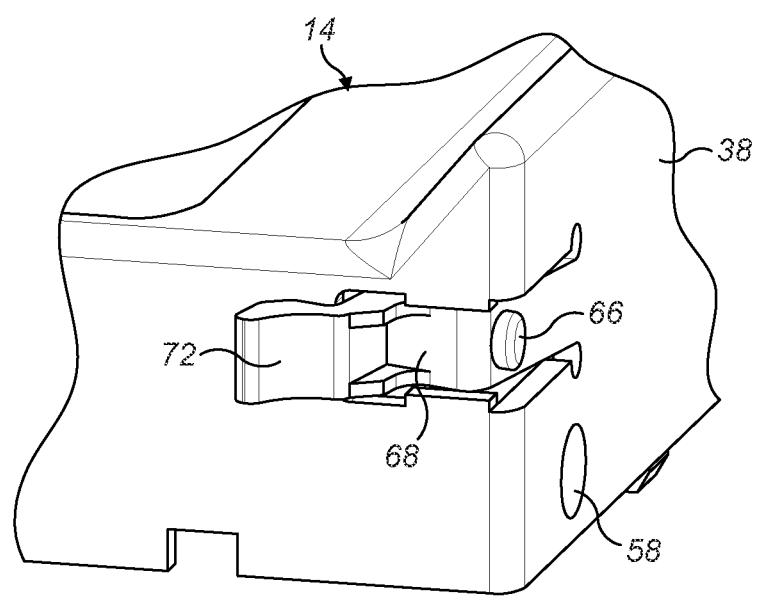
Figure 8:
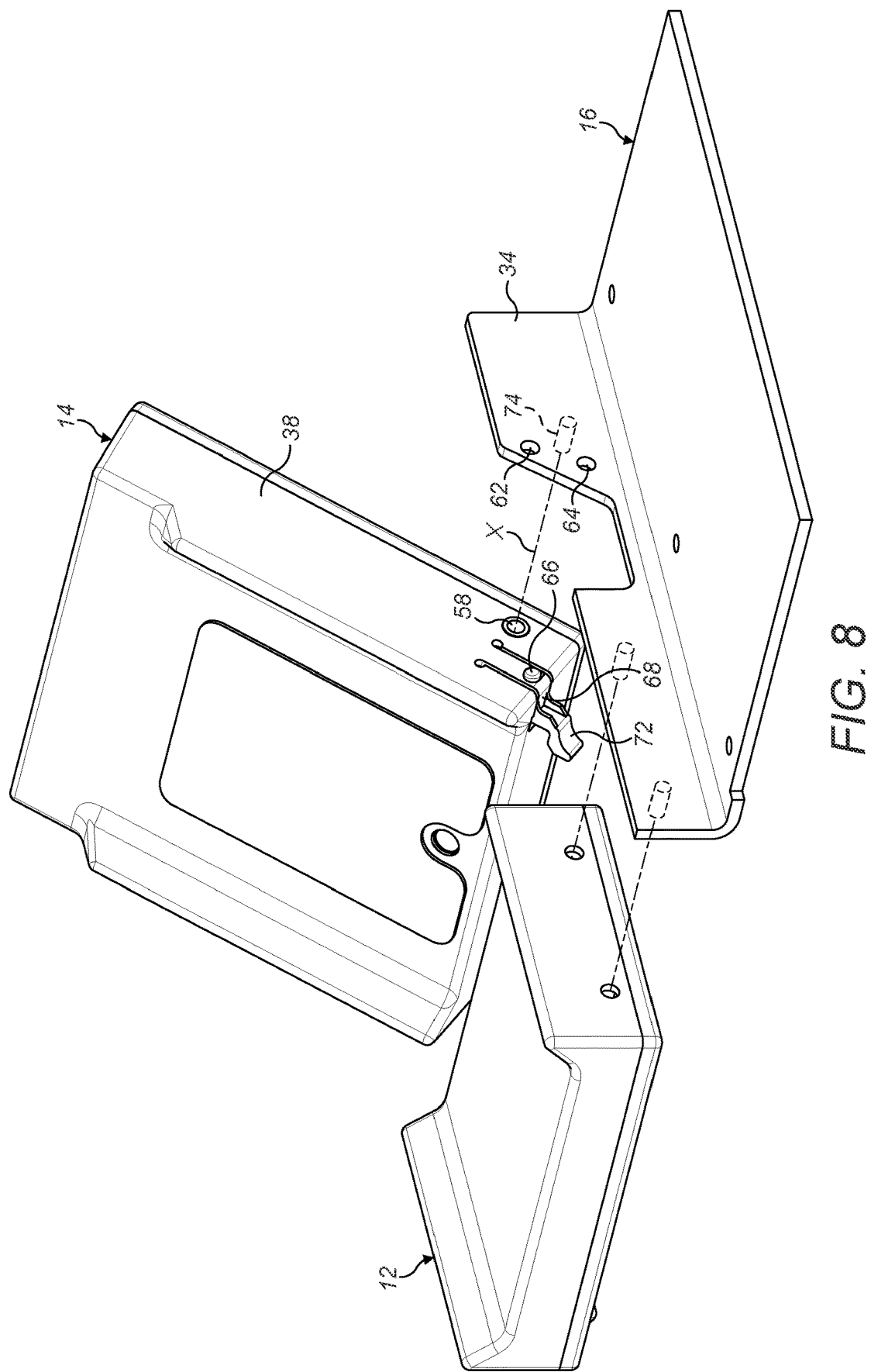
FIG. 8 is an exploded view of an adjustable support with the pivot mechanism of FIGS. 7A-B.

In the example shown in FIGS. 7A-B and 8, the attachment arm 16 is separate from the fixed tray 12 and can be attached to it with mechanical fasteners. The forward extension 34 is formed with upper and lower holes 62, 64 and the moveable tray 14 is formed with a projecting button 66 on a resilient lever arm 68. The lever arm 68 is integrally formed with the moveable tray 14 and defined by a slot 70 running around three edges of the arm 68. An extension on the end of the lever arm provides a grip 72 for the user. The moveable tray 14 is rotatably mounted on the attachment arm 16 by a pivot pin 74 secured to the attachment arm 16 which passes through the aperture 58 in the side wall 38 of the moveable tray 14.

When the moveable tray 14 is in the flat position, the projecting button 66 engages in the lower hole 64 to retain the tray 14 in that position. If a user pulls on the grip 72 the lever arm 68 flexes away from the attachment arm 16 and the button 66 releases from the hole 64, allowing the moveable tray 14 to rotate to the tilted position. Releasing the grip 72 allows the lever arm 68 to relax back towards the attachment arm 16 and engages the button 66 in the upper hole 62. The process is of course reversed to move the tray 14 back to the flat position.

To help support the weight of a bottle 24 when the holder 10 is in the tilted position, the moveable tray 14 may also include a flap or strut 54 which can fold out from its lower surface, as also shown in FIGS. 2 and 4. Such a flap 54 may be incorporated into a holder 10 with either form of pivot mechanism 20 described above. Alternatively, the moveable tray 14 may freely rotate on a pivot pin, without any additional form of catch or detent, and instead the flap 54 is simply deployed when the moveable tray 14 is tilted, or folded back against the lower surface of the moveable tray 14 when the latter is in the flat position.

Thus the present invention provides an adjustable holder which can be easily moved between alternative positions in order to support different forms of bottle.

The invention claimed is:

1. An adjustable bottle support for supporting a bottle for a pump, comprising a first support member having a flat base including a first bottle support surface, front, rear and side edges, an attachment arm extending from the first support member, and a second support member having a flat base including a second bottle support surface, front, rear and side edges, the second support member being secured to the attachment arm for pivotal movement relative to the first support member between a first position in which the first and second support surfaces lie in the same plane to contact and support the bottle, and a second position in which the second support member is tilted relative to the first support member and slopes upwardly in a direction away from the first support member and the rear edge of the second support member is lower than the front edge of the first support member, the first and second support members are configured to directly contact and support at least a portion of the bottle in both the first and second positions.

2. The adjustable bottle support as claimed in claim 1, wherein in the first position, the front edge of the first support member and the rear edge of the second support member are adjacent and level with each other, the second support member is rotatable about a pivot axis between its front and rear edges.

3. The adjustable bottle support as claimed in claim 2, wherein the first support member further comprises a downward sloping wall depending from the front edge.

4. The adjustable bottle support as claimed in claim 3, wherein in the second position, the angle between the base of the second support member and the downward sloping wall of the first support member is approximately 90 degrees.

5. The adjustable bottle support as claimed in claim 2, wherein the first support member further comprises a raised wall on the rear edge and at least one said side edge of the first support member.

6. The adjustable bottle support as claimed in claim 2, wherein the second support member further comprises side walls on opposed side edges.

7. The adjustable bottle support as claimed in claim 1, wherein the pivot mechanism comprises a pivot axle extending from the attachment arm on which the second support member is rotatably mounted, and a detent on the second support member selectively engageable with the attachment arm at first and second locations.

8. The adjustable bottle support as claimed in claim 7 wherein the detent comprises a resilient arm on the second support member with a projection selectively engageable with first and second openings in the attachment arm.

9. The adjustable bottle support as claimed in claim 8, wherein the resilient arm further comprises a grip portion protruding from the arm and operable by a user to selectively engage and disengage the projection with the first and second openings in the attachment arm.

10. The adjustable bottle support as claimed in claim 1, wherein the second support member further comprises a heating device operable to heat fluid in a bottle supported thereon.

11. The adjustable bottle support as claimed in claim 1, further comprising a flap attached to the second support member and moveable to a deployed position to hold the second support member in the second position.

12. An adjustable bottle support for a pump, comprising a first support member, an attachment arm extending from the first support member, and a second support member secured to the attachment arm for pivotal movement relative to the first support member between a first position in which the two support members are aligned and level with one another and a second position in which the second support member is tilted relative to the first support member and slopes upwardly in a direction away from the first support member, wherein the second support member is secured to the attachment arm by a pivot mechanism which comprises three pivot pins extending from the attachment arm and arranged in a triangular configuration, the pivot axis of the second support member passes through the centre of the triangular configuration, and a side wall of the second support member comprises three arcuate slots centred on the pivot axis, wherein each pivot pin extends through one of the slots.

13. The adjustable bottle support as claimed in claim 12, wherein each slot comprises first and second ends and a notch is formed at each end for receiving a pivot pin in the first and second positions respectively.

14. The adjustable bottle support as claimed in claim 13, wherein the notches are positioned such that in the first and second positions the weight of the second support member acts to retain each pin in a notch.

* * * * *